US00PP09090P

United States Patent [19]

Olesen et al.

[11] Patent Number: Plant 9,090

[45] Date of Patent: Mar. 28, 1995

[54] MINIATURE ROSE PLANT NAMED POULVOK

[75] Inventors: Mogens N. Olesen; Pernille Olesen, both of Fredensborg, Denmark

[73] Assignee: Bear Creek Gardens, Inc., Medford, Oreg.

[21] Appl. No.: 209,557

[22] Filed: Mar. 11, 1994

[51] Int. Cl.[6] ..... A01H 5/00

[52] U.S. Cl. ..... Plt./10

[58] Field of Search ..... Plt. 10, 10.1

*Primary Examiner*—Howard J. Locker

*Attorney, Agent, or Firm*—Klarquist Sparkman Campbell Leigh & Whinston

[57] ABSTRACT

A miniature rose plant having bright red flower color, compact dwarf growth habit, long shelf life, and ease of propagation from softwood cuttings.

1 Drawing Sheet

The present invention relates to a new and distinct variety of rose plant of the miniature class which was originated by us by crossing two unnamed seedlings.

The primary objective of this breeding was to produce a new rose variety having a dwarf, compact plant habit; ease of propagation from softwood cuttings; an attractive, clean, bright red flower color; and good shelf life as a pot or garden rose. The objective was substantially achieved, along with other desirable improvements, as evidenced by the following unique combination of characteristics that are outstanding in the new variety and that distinguish it from its parents, as well as from all other varieties of which we are aware:

1. Bright red, attractive flowers;
2. Compact dwarf habit;
3. Ease of propagation from softwood cuttings; and
4. Good pot rose shelf life.

Asexual reproduction of this new variety by softwood cuttings as performed at Wasco and Somis, Calif., and Fredensborg, Denmark, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of our new rose cultivar with color descriptions using terminology in accordance with The Royal Horticultural Society (London) Colour Chart, except where ordinary dictionary significance of color is indicated.

Parentage:

*Seed parent.*—Unnamed seedling.

*Pollen parent.*—Unnamed seedling.

Classification:

*Botanical.*—*Rosa hybrida.*

*Commercial.*—Miniature.

FLOWER

Observations made from specimens grown in greenhouse environments at Somis, Calif., and Fredensborg, Denmark.

Blooming habit: Continuous.

Bud:

*Size.*—1.3 cm inch long when the petals start to unfurl.

*Form.*—The bud form is short and globular.

*Color.*—When sepals first divide, bud color is Red Group 44A. When half blown, the upper and lower sides of the petals are Red Group 44A.

*Sepals.*—Color: Green Group 138B. Surface texture: Covered in fine hairs. There are three normally appendaged sepals. There are two unappendaged sepals with hairy edges.

*Receptacle.*—Color: Green Group 141C. Shape: Funnel. Size: Small (1 cm by 1 cm). Surface: Smooth.

*Peduncle.*—Length: Short (3.7 cm). Surface: Smooth. Color: Medium green. Strength: Stiff, erect.

Bloom:

*Size.*—Small. Average open size is 2.5 to 3 cm.

*Borne.*—Singly, several together, in flat clusters of 3 to 5 flowers.

*Stems.*—Short (13 cm); strong.

*Form.*—When first open: High centered. Permanence: Flattens, outer petals curl back, all petals curl.

*Petalage.*—Number of petals under normal conditions: 20 to 25.

*Color.*—The upper and reverse sides of the petals are Red Group 44A. The base of each petal has a very small, greenish-white half-moon at the point of attachment. The major color on the upper side is Red Group 44A.

*Variegations.*—None.

*Discoloration.*—The general tonality at the end of the first and third days: No change.

*Fragrance.*—Slight.

Petals:

*Texture.*—Thick.

*Shape.*—Deltoid.

*Form.*—Tips slightly recurved, edges slightly quilled.

*Arrangement.*—Imbricated, with few petaloids in the center.

*Persistence.*—Drop off cleanly.

*Lastingness.*—On the plant: Very long (14 to 16 days). As a cut-flower: Very long (10 days).

Reproductive parts:

*Anthers.*—Size: Small. Quantity: Many. Color: Yellow. Arrangement: Regular around styles.

*Filaments.*—Color: Yellow.
*Pollen.*—Color: Gold yellow.
*Styles.*—Color: Red.
*Stigmas.*—Color: Greenish white.

Form: Bush.
Growth: Vigorous, dwarf, upright, branching. Plant is 36 to 41 cm tall and 25 to 30 cm wide.

Foliage: Number of leaflets on normal mid-stem leaves: 5.
*Size.*—Small (6 cm×4 cm).
*Quantity.*—Normal.
*Color.*—New foliage: Green Group 137A. Old foliage: Green Group 139A.

Leaflets:
*Shape.*—Pointed oval.
*Texture.*—Upper side: Leathery, glossy.
*Edge.*—Serrated.
*Serration.*—Single, small.
*Petiole rachis.*—Color: Green.
*Petiole underside.*—Smooth, with occasional prickles.
*Stipules.*—Short, bearded.

*Disease resistance.*—Resistant to mildew and rust under normal growing conditions at Somis, Calif., and Fredensborg, Denmark.

Wood:
*New wood.*—Color: Light green. Bark: Smooth.
*Old wood.*—Color: Green. Bark: Smooth.

Prickles:
*Quantity.*—On main canes from base: Few. On laterals from main canes: Few.
*Form.*—Hooked slightly downward.
*Color when young.*—Green and red.

Small prickles:
*Quantity.*—On main stalks: None. On laterals: None.

We claim:

1. A new and distinct variety of rose plant of the miniature class, substantially as herein shown and described, characterized particularly as to novelty by the unique combination of its bright red flower color; compact, dwarf growth habit; long shelf life; and ease of propagation from softwood cuttings.

* * * * *

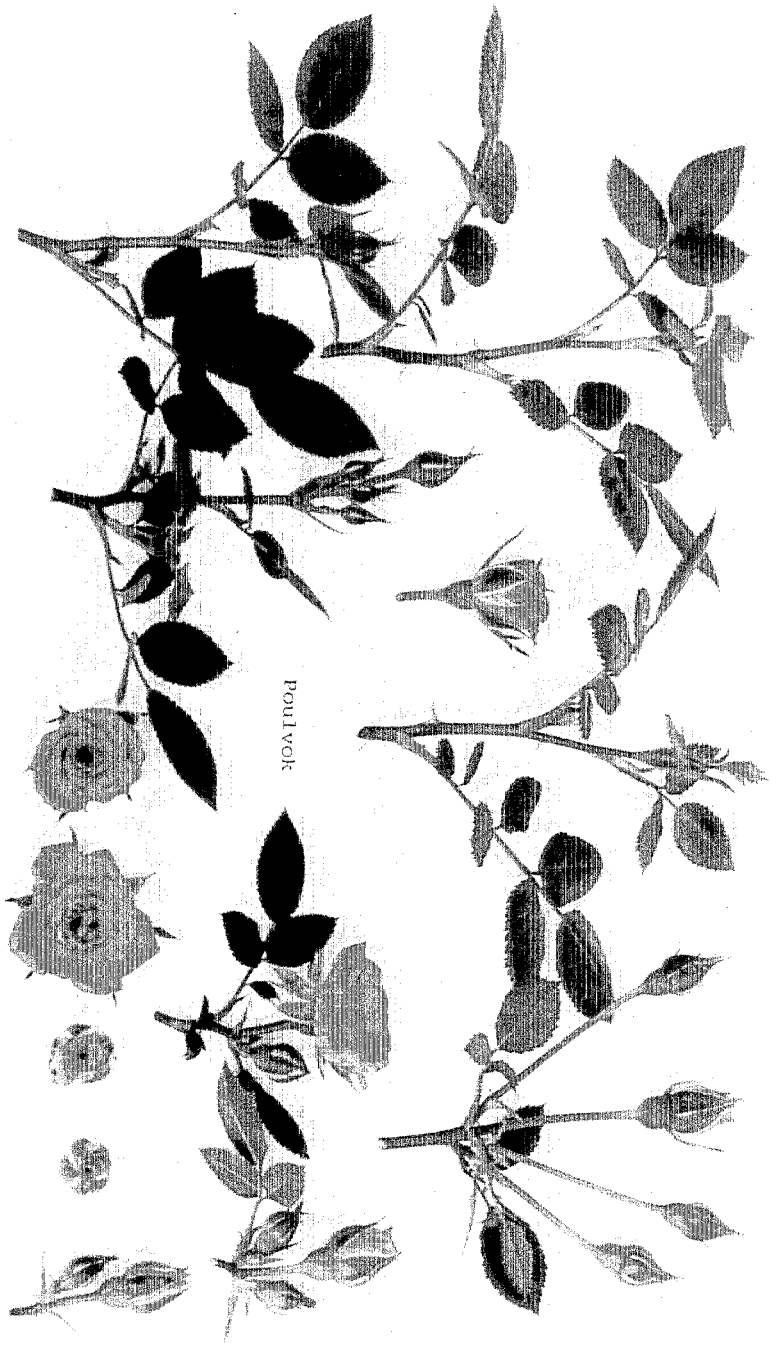
Paul Volk